United States Patent
Hanson et al.

(10) Patent No.: US 8,908,178 B1
(45) Date of Patent: Dec. 9, 2014

(54) METHOD FOR ATMOSPHERIC LASER BEAM DETECTION USING REMOTE SENSING OF OFF-AXIS SCATTERING

(71) Applicant: The United States of America as represented by the Secretary of the Navy, Washington, DC (US)

(72) Inventors: Frank E. Hanson, San Diego, CA (US); Charles S. Bendall, El Cajon, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 38 days.

(21) Appl. No.: 13/785,060

(22) Filed: Mar. 5, 2013

(51) Int. Cl.
*G01N 21/00* (2006.01)
*G01C 1/00* (2006.01)
*G01N 21/53* (2006.01)

(52) U.S. Cl.
CPC . *G01C 1/00* (2013.01); *G01N 21/53* (2013.01)
USPC .......... 356/343; 356/337; 356/614; 356/605; 356/519; 250/353; 250/334

(58) Field of Classification Search
CPC ... G01N 21/53; G01N 21/51; G01N 15/0205; G01N 21/47; G01N 15/1459; G01N 15/0211; G01N 15/0227; G01N 15/02; G01N 15/147; G01N 5/1459
USPC .......................... 356/434, 605, 614, 145, 622
See application file for complete search history.

(56) References Cited

U.S. PATENT DOCUMENTS

| | | | |
|---|---|---|---|
| 8,797,550 B2* | 8/2014 | Hays et al. | 356/519 |
| 8,810,796 B2* | 8/2014 | Hays et al. | 356/450 |
| 2005/0219554 A1* | 10/2005 | Tobiason et al. | 356/614 |
| 2007/0211258 A1* | 9/2007 | Lee et al. | 356/605 |
| 2012/0050750 A1* | 3/2012 | Hays et al. | 356/519 |
| 2012/0169053 A1* | 7/2012 | Tchoryk et al. | 290/44 |

OTHER PUBLICATIONS

Hanson, Frank E., et al., "Off-Axis Detection and Characterization of Laser Beams in the Maritime Atmopshere", Applied Optics, vol. 50, issue 18, pp. 3050-3056, 2011.

* cited by examiner

*Primary Examiner* — Tarifur Chowdhury
*Assistant Examiner* — Isiaka Akanbi
(74) *Attorney, Agent, or Firm* — SPAWAR Systems Center Pacific; Kyle Eppele; Ryan J. Friedl

(57) ABSTRACT

A method involves obtaining a first beam image on a focal plane of a first camera and a second beam image on a focal plane of a second camera from light scattered by ambient atmospheric aerosols in the path of a laser beam. First and second projected beam images are formed, representing the respective first and second beam images in the projected scenes of the respective first and second cameras. First and second ambiguity planes are then formed from the respective first and second projected beam images. An intersection of the first and second ambiguity planes is then determined, identifying the position of the laser beam. A source of the laser beam is then determined, along with a camera-source plane. A beam elevation angle with respect to this plane is then determined, as well as beam azimuth angles with respect to lines between the respective camera and the source.

20 Claims, 5 Drawing Sheets

METHOD FOR ATMOSPHERIC LASER BEAM DETECTION USING REMOTE SENSING OF OFF-AXIS SCATTERING

FEDERALLY-SPONSORED RESEARCH AND DEVELOPMENT

The Method for Atmospheric Laser Beam Detection Using Remote Sensing of Off-Axis Scattering is assigned to the United States Government and is available for licensing for commercial purposes. Licensing and technical inquiries may be directed to the Office of Research and Technical Applications, Space and Naval Warfare Systems Center, Pacific, Code 72120, San Diego, Calif., 92152; voice (619) 553-5118; email ssc_pac_T2@navy.mil; reference Navy Case Number 101726.

BACKGROUND

A traditional laser detection approach is to deploy an optical sensor on a platform and hope that in the event a laser illuminates the platform, the sensor will lie in the footprint of the laser. This is typically known as the direct detection approach, which is appropriate for small platforms and generally used in laser warning applications. Direct detection is impractical for very large platforms where the large number of sensors required to cover the platform would be cost prohibitive or for laser intelligence collection efforts where it is impractical or impossible to position a sensor in the beam path.

Accordingly, there would be significant value in being able to remotely determine the location and propagation direction of a laser beam including a continuous wave (CW) laser beam. This information could provide the location and range of the laser source as well as the intended target.

DETAILED DESCRIPTION OF SOME EMBODIMENTS

Reference in the specification to "one embodiment" or to "an embodiment" means that a particular feature, structure, or characteristic described in connection with the embodiments is included in at least one embodiment of the invention. The appearances of the phrases "in one embodiment", "in some embodiments", and "in other embodiments" in various places in the specification are not necessarily all referring to the same embodiment or the same set of embodiments.

The embodiments of the method disclosed herein determine the position and orientation of a laser beam propagating through the atmosphere by remote observation of off-axis scattering from aerosols in the beam path using two cameras. New features that are provided by this method are the position of the laser source, the direction of the laser beam, and an indication of the intended target. Unlike previous methods, this method will work for both pulsed and continuous-wave lasers.

Figure 1A:
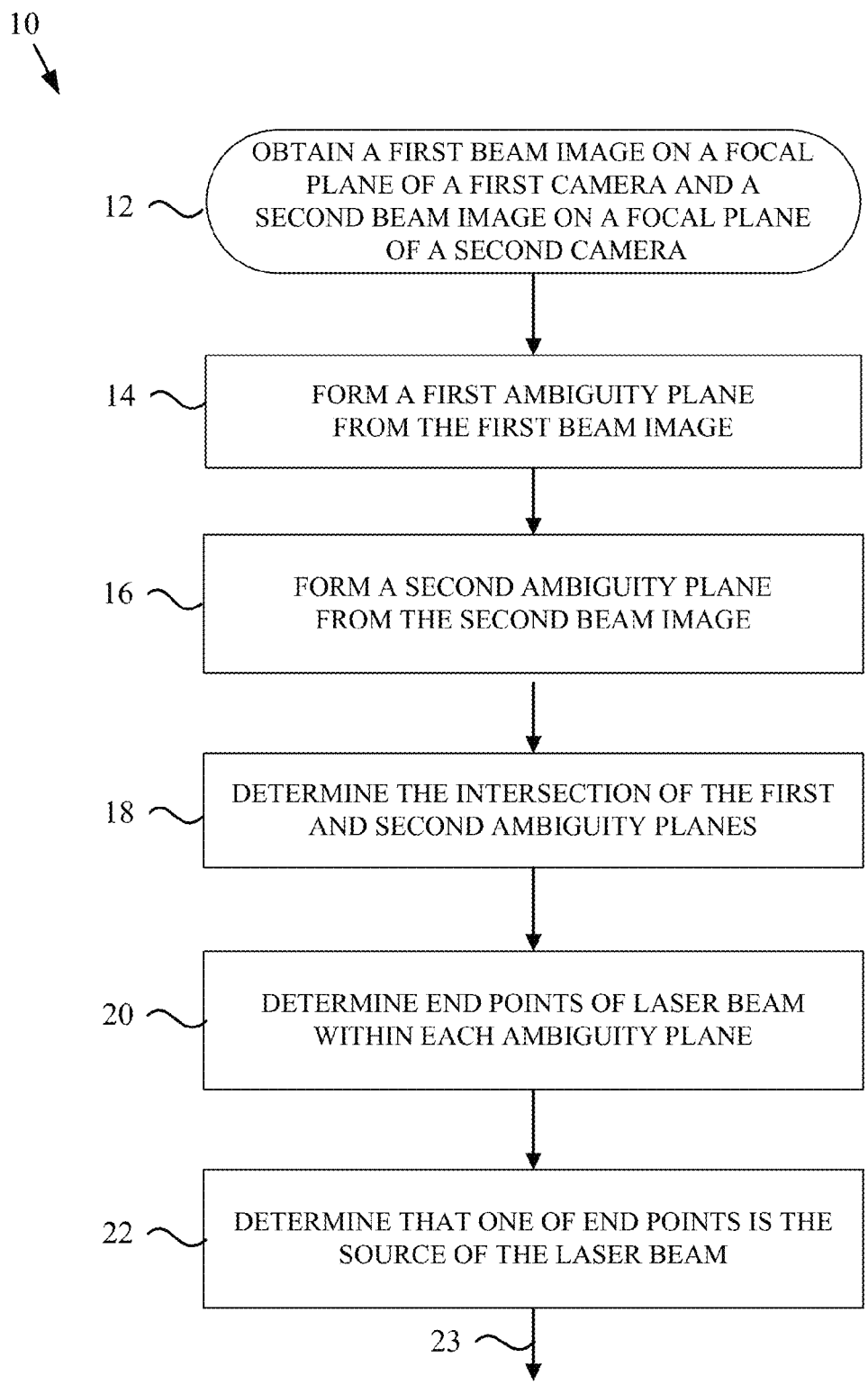
FIGS. 1A-1B show a flowchart of an embodiment of a method in accordance with the Method for Atmospheric Laser Beam Detection Using Remote Sensing of Off-Axis Scattering.
Figure 1B:
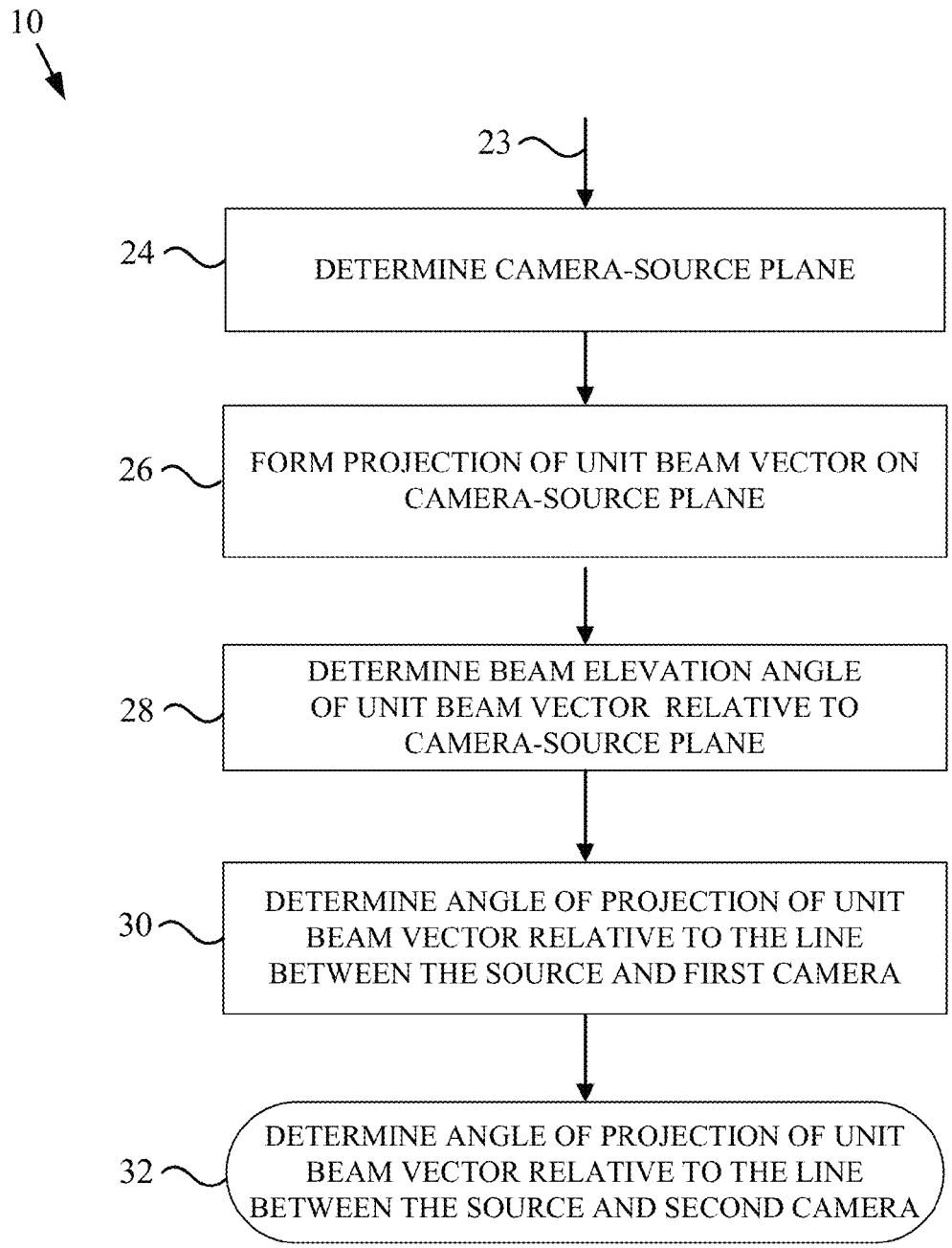
Figure 2:
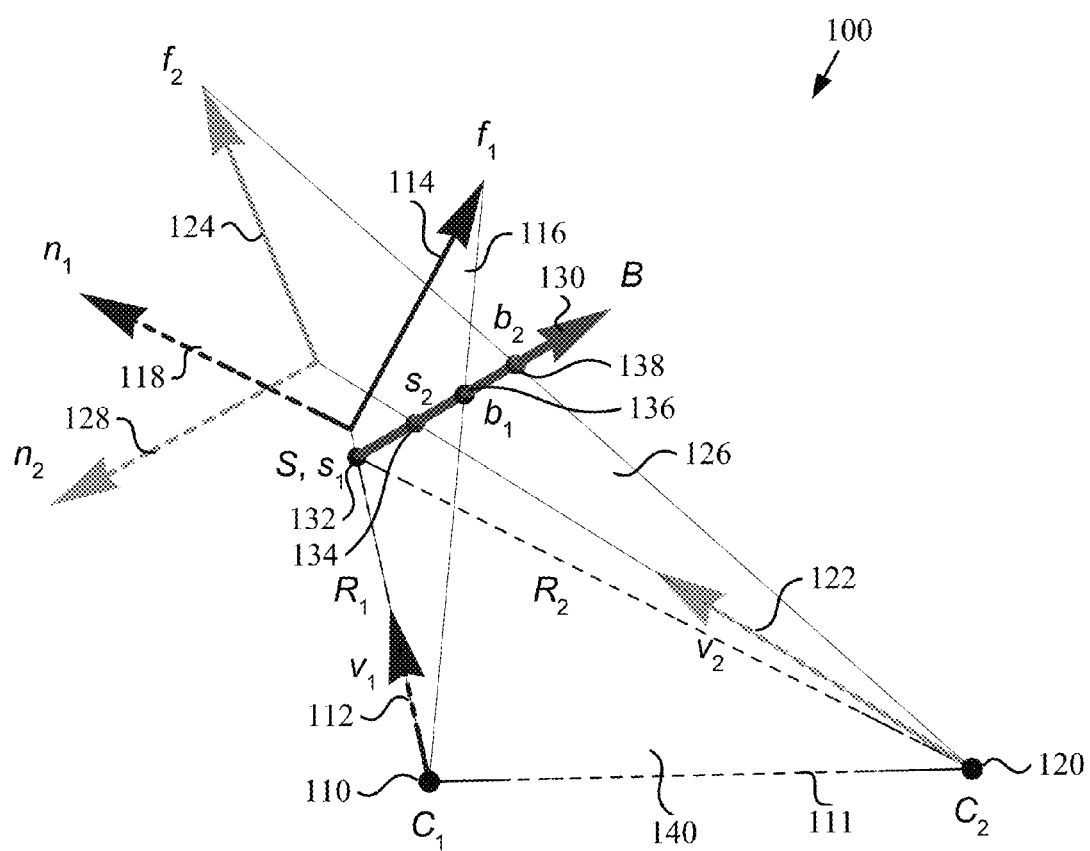
FIG. 2 shows a diagram illustrating the three-dimensional geometrical configuration of an embodiment of a system that may be used in accordance with the Method for Atmospheric Laser Beam Detection Using Remote Sensing of Off-Axis Scattering.
Figure 5:
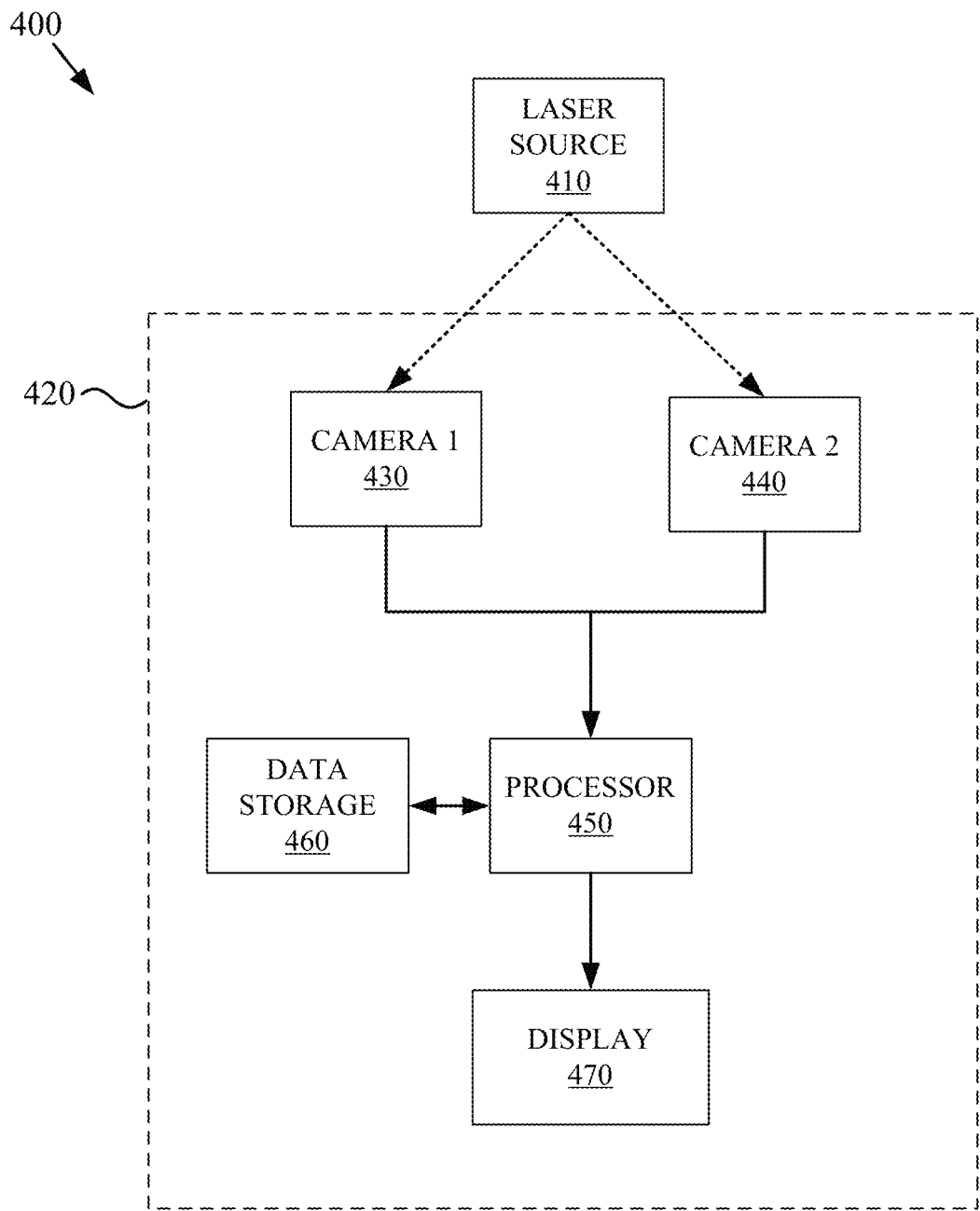
FIG. 5 shows a block diagram illustrating an embodiment of a system that may be used in accordance with the Method for Atmospheric Laser Beam Detection Using Remote Sensing of Off-Axis Scattering.

FIGS. 1A-1B show a flowchart of an embodiment of a method 10 in accordance with the Method for Atmospheric Laser Beam Detection Using Remote Sensing of Off-Axis Scattering. As an example, method 10 may be performed by system 100 as shown in FIG. 2 and system 400 as shown in FIG. 5. For illustration purposes, method 10 will be discussed with reference to system 100 and its respective components. Further, while FIGS. 1A and 1B show one embodiment of method 10 to include steps 12-32, other embodiments of method 10 may contain fewer or more steps. Further, while in some embodiments the steps of method 10 may be performed as shown in FIGS. 1A and 1B, in other embodiments the steps may be performed in a different order, or certain steps may occur simultaneously with one or more other steps.

A first aspect of one embodiment of method 10 involves a geometric approach. Accordingly, method 10 may begin at step 12, which involves obtaining a first beam image on a focal plane (not shown) of a first camera 110 and a second beam image on a focal plane (not shown) of a second camera 120 from light scattered by ambient atmospheric aerosols in the path of at least part of a laser beam 130. Referring to FIG. 2, a laser source S projects a laser beam B 130 through the atmosphere. First camera 110 located at point $C_1$ and a second camera 120 located at point $C_2$ are positioned in the direction of an expected laser beam and are oriented to allow them to form images on their respective focal planes of the light scattered from at least part of the beam by ambient aerosols in the beam path. Further, the distance separating cameras 110 and 120 and the orientation of each camera with respect to the line 111 separating them are known. That is, the orientation of the normal vector to the focal plane of camera 110 is known relative to line 111 and similarly for camera 120. Also, common access to information from both of cameras 110 and 120 is assumed.

It should be recognized that while some embodiments of method 10 utilize two cameras, other embodiments of method 10 may incorporate additional cameras. Further, the cameras are considered to be generic in nature and it is understood that their specific construction and operation might be optimized for a particular laser wavelength.

Step 14 then involves forming a first ambiguity plane 116 for the laser beam observed by the first camera. A projected beam image is formed that represents the first beam image in the projected scene of first camera 110. The part of laser beam B 130 passing through the field-of view (FOV) of camera 110 extends from $s_1$ 132 to $b_1$ 136. For clarity, the orientation of camera 110 is considered such that the projection plane in front of camera 110 is oriented perpendicular to the line from $C_1$ 110 to $s_1$ 132. In some embodiments however, other orientations and positions of the projection plane may be used. The projected image of this part of the beam is shown as vector $f_1$ 114. Another vector $v_1$ 112 is determined that points in the direction from $C_1$ 110 to $s_1$ 132.

These two vectors are contained within and define a first ambiguity plane 116 for laser beam 130 observed by camera 110 such that the laser beam 130 is known to lie within the first ambiguity plane 116. The information from camera 110 alone is insufficient to determine exactly where laser beam 130 lies within first ambiguity plane 116. A first normal vector $n_1$ 118, determined by the vector cross product $n_1 = f_1 \times v_1$, is normal to first ambiguity plane 116 and therefore to the laser beam B 130.

Step 16 involves forming a second ambiguity plane 126 for the laser beam 130 observed by the second camera. A projected beam image is formed that represents the second beam image in the projected scene of second camera 120. The part of laser beam B 130 passing through the field-of-view (FOV) of camera 120 extends from $s_2$ 134 to $b_2$ 138. For clarity the orientation of camera 120 is considered such that the projection plane in front of camera 120 is oriented perpendicular to the line from $C_2$ 120 to $s_2$ 134 In some embodiments however, other orientations and positions of the projection plane may be utilized. The projected image of the part of the beam is shown as vector $f_2$ 124. Another vector $v_2$ 122 is determined that points in the direction from $C_2$ 120 to $s_2$ 134. These two vectors are contained within and define a second ambiguity plane 126 for laser beam 130 observed by camera 120. A second normal vector $n_2$ 128, determined by the vector cross product $n_2 = f_2 \times v_2$, is normal to second ambiguity plane 126 and therefore to the laser beam B 130.

Step 18 then involves determining the intersection of first ambiguity plane 116 and second ambiguity plane 126. It is understood that because ambiguity planes 116 and 126 are infinite, the intersection line of ambiguity planes 116 and 126 is an infinite line. The laser beam B 130 is uniquely located within this intersection. As shown in FIG. 1, the portion of laser beam B passing through the field of view (FOV) of both cameras 110 and 120 is from point $s_2$ 134 to point $b_1$ 136.

In some embodiments, step 18 involves determining the orientation of the intersection and determining at least one of a point $s_1$ in the first ambiguity plane corresponding to the beginning of the laser beam within the first ambiguity plane and a point $s_2$ in the second ambiguity plane corresponding to the beginning of the laser beam within the second ambiguity plane. The step of determining an orientation of the intersection includes determining a first normal vector normal $n_1$ 118 to the first ambiguity plane 116, a second normal vector $n_2$ 128 normal to the second ambiguity plane 126, and a unit beam vector u formed by the cross product of the first normal vector $n_1$ 118 and the second normal vector $n_2$ 128. The direction of laser beam vector B 130 will therefore be parallel to a unit-vector u formed by $$u = n_1 \times n_2 / |n_1 \times n_2|. \quad (1)$$

The position of at least part of the laser beam B 130 is determined by finding, at step 20, at least one of the position of points $s_1$ 132 and $b_1$ 136 corresponding the end points of the part of laser beam B 130 passing through the field-of view (FOV) of camera 110 and of points $s_2$ 134 and $b_2$ 138 corresponding the end points of the part of laser beam B 130 passing through the field-of view (FOV) of camera 120. The point $s_1$ 132 can be calculated as $$s_1 = C_1 + v_1[(C_2 - C_1) \cdot n_2]/[v_1 \cdot n_2] \quad (2)$$

and the point $s_2$ 134 can be calculated as $$s_2 = C_2 + v_2[(C_1 - C_2) \cdot n_1]/[v_2 \cdot n_1] \quad (3)$$

A similar calculation could be used to determine the position of $b_1$ 136 and $b_2$ 138.

These end points are not necessarily the position of laser source S, since it has not been determined that the laser beam source S lies within the FOV of either camera 110 or 120. Accordingly, step 22 involves determining if any of these end points correspond to the position of the laser source S. Other information in the scene of each camera will generally be available to determine if the source or perhaps a target has been imaged by cameras 110 and 120. For example, if either of the end points $s_1$ 132 or $b_1$ 136 lie on the perimeter of the FOV of camera 110 they would not be considered the position of the source S and similarly for camera 120. In this case, the FOV of the camera could be adjusted to encompass a different part of the beam. Assuming there are no objects in the scene to obstruct the laser beam source S, it will generally be very much brighter than all other points along the beam due to scattering from optical elements in the laser transmitter. The diagram shown in FIG. 2 illustrates that the laser beam source S lies within the FOV of camera 110, but not within the FOV of camera 120, thus $s_1$ 132 and S are the same point.

The following discussion is premised upon the laser beam source S having been imaged by at least one of cameras 110 and 120. Method 10 may then proceed along flow path 23 to step 24, where a camera-source plane 140 is determined. It is evident that the configuration of the triangle formed by $C_1$ 110, S 132, and $C_2$ 120 can be completely determined, such with the plane of the triangle referred to as the camera-source plane 140. In particular, the distances $R_1$ from S 132 to $C_1$ 110, $R_2$ from S 132 to $C_2$ 120, and the angle $\phi_C$ formed between the line from S 132 to $C_1$ 110 and the line from S 132 to $C_2$ 120 can be determined. A common three-dimensional coordinate system based on the plane of this triangle with the origin at S 132 is used and all vectors are considered in such a coordinate system.

Figure 3:
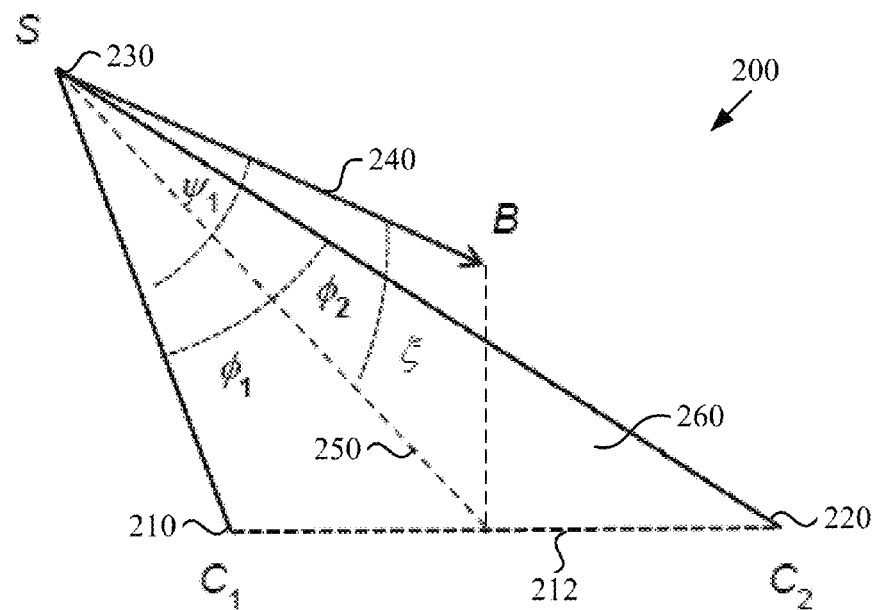
FIG. 3 shows a diagram illustrating the beam elevation angle defined relative to a camera-source plane of the system shown in FIG. 2.

Referring to FIG. 3, FIG. 3 is an alternative representation of the three-dimensional geometry shown in FIG. 2 and shows a diagram 200 of a first camera 210 positioned relative to a second camera 220 and a laser source 230, which projects a laser beam vector B 240. Beam vector B 240 can be described by a beam elevation angle $\xi$ from the camera-source plane 260 formed by S 230, $C_1$ 210, and $C_2$ 220, and an azimuthal angle $\phi_1$ relative to the line from S 230 to $C_1$ 210 or angle $\phi_2$ relative to the line from S 230 to $C_2$ 220. Beam vector B 240 is directed at a beam angle $\psi_1$ to the line from S 230 to $C_1$ 210 and a beam angle $\psi_2$ (not shown) to the line from S 230 to $C_2$ 220.

Step 26 of method 10 involves forming a projection 250 of the unit beam vector 240 from S 230 onto the camera-source plane 260. Step 28 then involves determining the beam elevation angle $\xi$ of the beam unit vector 240 relative to camera-source plane 260. Step 30 involves determining a first beam azimuth angle $\phi_1$ corresponding to the angle of the projection of unit beam vector 240 relative to the line from S 230 to $C_1$ 210. Step 32 then involves determining a second beam azimuth angle $\phi_2$ corresponding the angle of projection of unit beam vector 240 relative to the line from S 230 to $C_2$ 220. Angle $\phi_2$ may be determined by $\phi_2 = \phi_1 - \phi_C$, where these angles are taken to be positive in the counter-clockwise direction.

A problem with the determination of the beam direction based on Eq. (1) will arise if the elevation angle $\xi$ of the beam is small compared to both $\phi_1$ and $\phi_2$. In this situation, as $\xi$ approaches zero, ambiguity planes 116 and 126 shown in FIG. 2 become closer to parallel and the magnitude $|n_1 \times n_2|$ approaches zero. It can be shown that the uncertainty in the determination of either $\phi_1$ or $\phi_2$ will diverge as $\xi$ approaches zero. When the beam elevation $\xi$ is equal to zero, the geometric method will not provide reliable information about the azimuthal direction of the laser beam.

Figure 4:
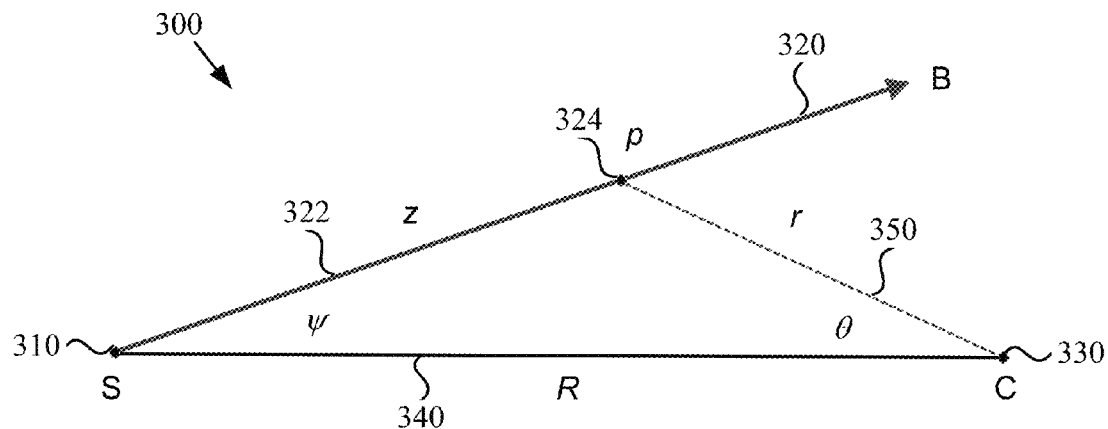
FIG. 4 shows a diagram illustrating the scattering geometry in the camera-source plane of the system shown in FIG. 2 when the beam elevation angle is near zero.

When the beam elevation $\xi$ is close to zero, additional steps based on the variation of intensity of the beam images in the cameras 110 and 120 may be needed to help determine the beam azimuth angles. Referring to FIG. 4, FIG. 4 shows a diagram 300 of the scattering geometry in the scattering plane formed by the source S 310, the beam vector B 320 and the camera C 330. Source 310 and camera 330 are separated by a distance R. Scattering occurs at point p 324 at a distance z 322 from S and a distance r 350 from C. B is inclined at a beam angle ψ r relative to the baseline from source S 310 to C 330. The scattering from point p 324 is observed at C 330 at angle θ relative to the baseline. The radiance L of scattered light in this plane at the aperture of camera 330 is given by $$L(\theta) = P_0 T(z, r) \frac{\beta(\psi + \theta)}{R \sin(\psi)} \quad (4)$$

if multiple scattering is neglected (see "Off-axis detection and characterization of laser beams in the maritime atmosphere," Hanson et al., Appl. Opt. 50, 3050-3056 (2011)). Here $P_0$ is the initial laser power and R 340 is the distance from source S 310 to camera 330. $\beta(\psi+\theta)$ is the volume scattering function due to aerosols or other particles in the beam path and the beam angle ψ is the angle of the beam with respect to the line from source to camera. It is assumed that the atmosphere is uniform and therefore the scattering function is independent of position. The transmission T(z,r) of light along the path of the beam from source S 310 to the scattering point p and from that point to the camera C is given by $$T(z,r) = \exp[-\alpha(z+r)] \quad (5)$$

Where α=(a+b) is the extinction coefficient due to absorption plus scattering and the distances z and r are implicit functions of ψ and θ according to $$z = R \frac{\sin(\theta)}{\sin(\psi + \theta)} \quad (6)$$

$$r = R \frac{\sin(\psi)}{\sin(\psi + \theta)} \quad (7)$$

It is valid to neglect multiple scattering if b(r+z)<<1 where b is the component of α due to scattering alone.

The angular dependence of radiance in Eq. (4) on scattering angle θ is primarily due to the scattering function $\beta(\psi+\theta)$ which is generally a strongly decreasing function of angle for angles less than ~90°. The details of the scattering function β are not generally known. However if the ratio of the radiance at both cameras, such as cameras 110 and 120 shown in FIG. 2, is taken with the appropriate angular offset $\Delta\psi=\psi_1-\psi_2$, the scattering functions will be equal and cancel, $$\frac{L_1(\theta)}{L_2(\theta + \psi_1 - \psi_2)} = \frac{R_2 \sin(\psi_2)}{R_1 \sin(\psi_1)} \exp[-\alpha(z_1 - z_2 + r_1 - r_2)]. \quad (8)$$

The beam angles $\psi f_1$ and $\psi_2$ relative to the two cameras are related to the beam elevation angle ξ and azimuthal angles according to $$\cos(\psi_1) = \cos(\xi)\cos(\phi_1) \quad (9)$$

and $$\cos(\psi_2) = \cos(\xi)\cos(\phi_1 - \phi_C). \quad (10)$$

The distances $R_1$ and $R_2$ and the beam elevation ξ are determined from the geometric method and therefore, apart from the extinction term, Eq. (8) only involves one unknown, $\phi_1$.

The measured signal from each camera along the beam image can be converted to a value Y proportional to radiance L by taking into account various specific parameters of the cameras including the response and orientation of the camera with respect the direction of the scattering. It is only important that the proportionality to actual radiance be the same for each camera. Therefore we can replace the left side of Eq. (8) with measured quantities, $$\frac{Y_1(\theta)}{Y_2(\theta + \psi_1 - \psi_2)} \approx \frac{R_2 \sin(\psi_2)}{R_1 \sin(\psi_1)} \exp[-\alpha(z_1 - z_2 + r_1 - r_2)]. \quad (11)$$

An error function $\chi^2$ that depends parametrically on $\phi_1$ and α is formed by summing over camera pixels i along the beam images, $$\chi^2(\phi_1, \alpha) = \quad (12)$$

$$\frac{1}{n} \sum_i^n \left[ \frac{Y_1(\theta_i)}{Y_2(\theta_i + \psi_1 - \psi_2)} - \frac{R_2 \sin(\psi_2)}{R_1 \sin(\psi_1)} \exp[-\alpha(z_1 - z_2 + r_1 - r_2)] \right]^2,$$

where z and r are implicit functions of θ and $\phi_1$. An estimated azimuthal beam angle $\phi_1$ is obtained by minimizing $\chi^2$ with respect to $\phi_1$ for a given α. In many cases the product of α and the difference in path length will be much less than unity and therefore the estimate of beam angle will not be sensitive to α. A best estimate $\phi_R$ of beam azimuth angle $\phi_1$ based on scattered radiance is determined using the best estimate of α based on weather conditions including meteorological range or visibility measurements.

In some embodiments, the final determination of beam azimuth angles in steps 30 and 32 is made using information from both the geometric analysis and the radiance analysis. Each analysis will have some uncertainty, for example from errors in camera position and orientation and measured radiance. In particular, the uncertainty $\sigma_G$ and $\sigma_R$ in beam azimuth angle can be estimated for the geometric and radiance analysis respectively. The final determination of beam azimuth angle might be the weighted average of the azimuth angles $\phi_G$ and $\phi_R$ obtained from the geometric and radiance analysis respectively, $$\phi = \left( \frac{\phi_G}{\sigma_G^2} + \frac{\phi_R}{\sigma_R^2} \right) / \left( \frac{1}{\sigma_G^2} + \frac{1}{\sigma_R^2} \right). \quad (13)$$

Some or all of the steps of method 10 may be stored on a computer-readable storage medium, such as a non-transitory computer-readable storage medium, wherein the steps are represented by computer-readable programming code. The steps of method 10 may also be computer-implemented using a programmable device, such as a computer-based system. Method 10 may comprise instructions that may be stored within a processor or may be loaded into a computer-based system, such that the processor or computer-based system then may execute the steps of method 10. Method 10 may be implemented using various programming languages, such as "Java", "C" or "C++".

Various storage media, such as magnetic computer disks, optical disks, and electronic memories, as well as non-transitory computer readable storage media and computer program products, can be prepared that can contain information that can direct a device, such as a micro-controller or processor, to implement method 10. Once an appropriate device has access to the information and programs contained on the storage media, the storage media can provide the information and programs to the device, enabling the device to perform the above-described systems and/or methods.

For example, if a computer disk containing appropriate materials, such as a source file, an object file, or an executable file, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods, and coordinate the functions of the individual systems and/or methods.

FIG. 5 shows a diagram 400 of an embodiment of a system that may be used in accordance with the embodiments of method 10 discussed herein. As shown, a laser source 410 transmits a laser beam into the atmosphere. Light scattered by ambient atmospheric aerosols in the path of the laser beam is captured by system 420, particularly on the focal planes of a first camera 430 and a second camera 440 contained within system 420. As an example, cameras 430 and 440 may be digital video cameras or any other camera suitable for the purposes described herein as recognized by one having ordinary skill in the art.

Cameras 430 and 440 are connected to a processor 450, which receives input from cameras 430 and 440 and performs the various calculations and determinations of method 10 as discussed above. Processor 450 may include computer-implementable instructions represented by computer-readable programming code stored therein, with such instructions configured to perform the steps of method 10. Processor 450 may be any device configured to perform computations on the input received from cameras 430 and 440. For example, processor 450 may be a commercially available computing device that has been modified to include programming instructions therein to allow processor 450 to perform the steps of method 10.

A data storage device 460 may connected to processor 450. Data storage 460 may contain data and/or instructions stored therein for use by processor 450 in performing some or all of the steps of method 10. As an example, data storage device 460 may be any standard memory device, such as EEPROM, EPROM, RAM, DRAM, SDRAM, or the like. Input data, as received from cameras 430 and 440, may be stored in data storage 460 in various ways, such as in a table format or other format as recognized by one having ordinary skill in the art. Processor 450 may be configured to provide an output to display 470. In some embodiments, such output may include the position of the laser beam source, the direction of propagation of the laser beam, and an indication of the intended target of the laser beam. Display 470 may comprise any commercially available display. As an example, display 470 may be liquid crystal display.

Many modifications and variations of the Method for Atmospheric Laser Beam Detection Using Remote Sensing of Off-Axis Scattering are possible in light of the above description. Within the scope of the appended claims, the embodiments of the subject matter described herein may be practiced otherwise than as specifically described. The scope of the claims is not limited to the implementations and the embodiments disclosed herein, but extends to other implementations and embodiments as may be contemplated by those persons having ordinary skill in the art.

We claim:

1. A method comprising the steps of:
using a first camera to obtain a first beam image on a focal plane of the first camera and using a second camera to obtain a second beam image on a focal plane of the second camera from light scattered by ambient atmospheric aerosols in the path of at least part of a laser beam;
forming a first projected beam image that represents the first beam image in the projected scene of the first camera;
forming a second projected beam image that represents the second beam image in the projected scene of the second camera;
forming a first ambiguity plane from the first projected beam image;
forming a second ambiguity plane from the second projected beam image; and
determining an intersection of the first ambiguity plane and the second ambiguity plane, wherein at least a portion of the laser beam is located within the intersection.

2. The method of claim 1 wherein the step of forming the first ambiguity plane comprises the steps of:
determining a first vector representing the first projected beam image; and
determining a second vector representing the direction from the first camera to the beginning of the first vector, wherein the first ambiguity plane is defined by the first vector and the second vector.

3. The method of claim 2 wherein the step of forming the second ambiguity plane comprises the steps of:
determining a third vector representing the second projected beam image; and
determining a fourth vector representing the direction from the second camera to the beginning of the third vector, wherein the second ambiguity plane is defined by the third vector and the fourth vector.

4. The method of claim 1, wherein the step of determining the intersection of the first ambiguity plane and the second ambiguity plane comprises the steps of:
determining the orientation of the intersection; and
determining at least one of a point $s_1$ in the first ambiguity plane corresponding to the beginning of the laser beam within the first ambiguity plane and a point $s_2$ in the second ambiguity plane corresponding to the beginning of the laser beam within the second ambiguity plane.

5. The method of claim 4, wherein the step of determining an orientation of the intersection comprises:
determining a first normal vector normal to the first ambiguity plane;
determining a second normal vector normal to the second ambiguity plane; and
determining a unit beam vector formed by the cross product of the first normal vector and the second normal vector, wherein the intersection is parallel to the unit beam vector.

6. The method of claim 4, wherein the step of determining the position of at least one of a point $s_1$ and $s_2$ is performed according to $s_1=C_1+v_1[(C_2-C_1)\cdot n_2]/[v_1\cdot n_2]$ and $s_2=C_2+v_2[(C_1-C_2)\cdot n_1]/[v_2\cdot n_1]$, where $C_1$ is the position of the first camera, $C_2$ is the position of the second camera, $v_1$ is the first vector, $v_2$ is the second vector, $n_1$ is the first normal vector, and $n_2$ is the second normal vector.

7. The method of claim 6 further comprising the step of determining that one of $s_1$ and $s_2$ corresponds to the position S of a laser beam source based on at least one of a termination of the laser beam in an unobstructed scene and an enhanced brightness in one of the respective first projected beam image and the second projected beam image due to scattering from optical elements of the laser beam source.

8. The method of claim 7 further comprising the steps of:
determining a camera-source plane formed by positions S, $C_1$, and $C_2$;
forming a projection of the unit beam vector from S onto the camera-source plane;
determining a beam elevation angle of the beam unit vector relative to the camera-source plane;
determining a first beam azimuth angle $\phi_1$ corresponding the angle of the projection of the unit beam vector relative to the line from S to $C_1$; and
determining the second beam azimuth angle $\phi_2$ corresponding the angle of the projection of the unit beam vector relative to the line from S to $C_2$.

9. The method of claim 8 wherein the steps of determining the first and the second beam azimuth angles are based upon variation of radiance of the first beam image and the second beam image, wherein the beam angle of the laser beam is determined using the equation $$L(\theta) = P_0 T(z, r) \frac{\beta(\psi + \theta)}{R \sin(\psi)},$$

where L is the one-dimensional radiance of scattered light at the aperture of the first and the second cameras, $\theta$ is the angle of received light, from scattering at point p along the beam path, at the respective first and second camera with respect to the direction of the laser source, $P_0$ is the initial laser power, R is the distance from the respective camera to the laser source, $\beta(\psi+\theta)$ is the volume scattering function due to aerosols or other particles in the path of the laser beam, $\psi$ is the beam angle of the laser beam with respect to the line from the laser source to the respective camera, and T(z,r) represents the transmission of light along the path of the laser beam from the laser source to a scattering point p and from the scattering point p to the respective camera.

10. The method of claim 9 further comprising the step of converting a measured signal in the beam image from each of the first and second cameras to a scaled radiance Y($\theta$) that is proportional to radiance and the dependence of scaled radiance on a scattering angle $\theta$ is obtained.

11. The method of claim 10, wherein the first and the second beam azimuth angles are determined by finding a solution to the equation $$\frac{Y_1(\theta)}{Y_2(\theta + \psi_1 - \psi_2)} = \frac{R_2 \sin(\psi_2)}{R_1 \sin(\psi_1)} \frac{T_1}{T_2}.$$

12. A system comprising:
a first camera and a second camera; and
a processor operatively connected to both the first and second cameras, the processor having computer-implementable instructions represented by computer-readable programming code stored therein, the processor configured to perform the steps of:
using a first camera to obtain a first beam image on a focal plane of the first camera and using a second camera to obtain a second beam image on a focal plane of the second camera from light scattered by ambient atmospheric aerosols in the path of at least part of a laser beam,
forming a first projected beam image that represents the first beam image in the projected scene of the first camera,
forming a second projected beam image that represents the second beam image in the projected scene of the second camera,
forming a first ambiguity plane from the first projected beam image,
forming a second ambiguity plane from the second projected beam image, and
determining an intersection of the first ambiguity plane and the second ambiguity plane, wherein at least a portion of the laser beam is located within the intersection.

13. The system of claim 12 wherein the step of forming the first ambiguity plane comprises the steps of determining a first vector representing the first projected beam image and determining a second vector representing the direction from the first camera to the beginning of the first vector, wherein the first ambiguity plane is defined by the first vector and the second vector, and the step of forming the second ambiguity plane comprises the steps of determining a third vector representing the second projected beam image and determining a fourth vector representing the direction from the second camera to the beginning of the third vector, wherein the second ambiguity plane is defined by the third vector and the fourth vector.

14. The system of claim 12, wherein the step of determining the intersection of the first ambiguity plane and the second ambiguity plane comprises the steps of:
determining the orientation of the intersection; and
determining at least one of a point $s_1$ in the first ambiguity plane corresponding to the beginning of the laser beam within the first ambiguity plane and a point $s_2$ in the second ambiguity plane corresponding to the beginning of the laser beam within the second ambiguity plane.

15. The system of claim 14, wherein the step of determining the orientation of the intersection comprises the steps of:
determining a first normal vector normal to the first ambiguity plane;
determining a second normal vector normal to the second ambiguity plane; and
determining a unit beam vector formed by the cross product of the first normal vector and the second normal vector, wherein the laser beam is parallel to the unit beam vector.

16. The system of claim 14, wherein the step of determining the position of at least one of a point $s_1$ and $s_2$ is performed according to $s_1 = C_1 + v_1[(C_2 - C_1) \cdot n_2]/[v_1 \cdot n_2]$ and $s_2 = C_2 + v_2[(C_1 - C_2) \cdot n_1]/[v_2 \cdot n_1]$, where $C_1$ is the position of the first camera, $C_2$ is the position of the second camera, $v_1$ is the first vector, $v_2$ is the second vector, $n_1$ is the first normal vector, and $n_2$ is the second normal vector.

17. The system of claim 16, wherein the processor is further configured to perform the step of determining that one of $s_1$ and $s_2$ corresponds to the position S of a laser beam source based on at least one of a termination of the laser beam in an unobstructed scene and an enhanced brightness in one of the respective first projected beam image and the second projected beam image due to scattering from optical elements of the laser beam.

18. The system of claim 17, wherein the processor is further configured to perform the steps of:
determining a camera-source plane formed by positions S, $C_1$, and $C_2$;
forming a projection of the unit beam vector from S onto the camera-source plane;

determining a beam elevation angle of the beam unit vector relative to the camera-source plane;

determining a first beam azimuth angle $\phi_1$ corresponding the angle of the projection of the unit beam vector relative to the line from S to $C_1$; and determining the second beam azimuth angle $\phi_2$ corresponding the angle of the projection of the unit beam vector relative to the line from S to $C_2$, wherein the steps of determining the first and the second beam azimuth angles are based upon variation of radiance of the first beam image and the second beam image.

19. The system of claim 18, wherein the beam angle of the laser beam is determined using the equation $$L(\theta) = P_0 T(z, r) \frac{\beta(\psi + \theta)}{R \sin(\psi)},$$

where L is the one-dimensional radiance of scattered light at the aperture of the first and the second cameras, $\theta$ is the angle of received light, from scattering at point p along the beam path, at the respective first and second camera with respect to the direction of the laser source, $P_0$ is the initial laser power, R is the distance from the respective camera to the laser source, $\beta(\psi+\theta)$ is the volume scattering function due to aerosols or other particles in the path of the laser beam, $\psi$ is the beam angle of the laser beam with respect to the line from the laser source to the respective camera, and T(z,r) represents the transmission of light along the path of the laser beam from the laser source to a scattering point p and from the scattering point p to the respective camera.

20. The system of claim 19, wherein the processor is further configured to perform the step of converting a measured signal in the beam image from each of the first and second cameras to a scaled radiance $Y(\theta)$ that is proportional to radiance and the dependence of scaled radiance on a scattering angle $\theta$ is obtained, wherein the first and the second beam azimuth angles are determined by finding a solution to the equation $$\frac{Y_1(\theta)}{Y_2(\theta + \psi_1 - \psi_2)} = \frac{R_2 \sin(\psi_2)}{R_1 \sin(\psi_1)} \frac{T_1}{T_2}.$$

\* \* \* \* \*